US012570681B2

(12) United States Patent
Zhang et al.

(10) Patent No.: US 12,570,681 B2
(45) Date of Patent: Mar. 10, 2026

(54) PRODUCTION APPARATUS AND PRODUCTION METHOD OF SUCROSE-6-ESTER

(71) Applicant: ANHUI JINHE INDUSTRIAL CO., LTD., Chuzhou (CN)

(72) Inventors: Zhengsong Zhang, Chuzhou (CN); Zhenghua Li, Chuzhou (CN); Jingang Zhao, Chuzhou (CN); Congyong Zhang, Chuzhou (CN); Xuelian Zheng, Chuzhou (CN); Yongfeng Bu, Chuzhou (CN)

(73) Assignee: ANHUI JINHE INDUSTRIAL CO., LTD., Chuzhou (CN)

( * ) Notice: Subject to any disclaimer, the term of this patent is extended or adjusted under 35 U.S.C. 154(b) by 224 days.

(21) Appl. No.: 18/002,467

(22) PCT Filed: Feb. 7, 2021

(86) PCT No.: PCT/CN2021/075813
§ 371 (c)(1),
(2) Date: Dec. 19, 2022

(87) PCT Pub. No.: WO2022/165803
PCT Pub. Date: Aug. 11, 2022

(65) Prior Publication Data
US 2023/0399352 A1 Dec. 14, 2023

(51) Int. Cl.
*B01D 3/08* (2006.01)
*B01D 3/00* (2006.01)
(Continued)

(52) U.S. Cl.
CPC ............. *C07H 13/04* (2013.01); *B01D 3/009* (2013.01); *B01D 3/08* (2013.01); *B01D 3/34* (2013.01); *B01D 5/006* (2013.01)

(58) Field of Classification Search
CPC . B01D 3/009; B01D 3/08; B01D 3/34; B01D 5/006; C07H 13/04
See application file for complete search history.

(56) References Cited

U.S. PATENT DOCUMENTS 4,311,570 A * 1/1982 Cowen ................... C08G 63/54
423/604
5,530,106 A * 6/1996 Navia .................... C07H 13/08
536/127
(Continued)

FOREIGN PATENT DOCUMENTS

CN 1431214 A 7/2003
CN 102639551 A 8/2012
(Continued)

*Primary Examiner* — Jonathan Miller

(57) ABSTRACT

A production apparatus and a production method of sucrose-6-ester are provided. The production apparatus includes a tank, a rotary distillation device, and a condensation device, the tank includes a separation chamber and a reaction chamber; the condensation device is sheathed inside the rotary distillation device, and the rotary distillation device is slidably connected in the separation chamber; a turntable of the rotary distillation device is fixed on a top surface of a drum, and a first heating device is provided on an outer wall of the turntable; the condensation device includes a condenser pipe, a water receiving plate, and a condensate water box that are connected sequentially from top to bottom; the condensation device is sheathed inside the drum of the rotary distillation device in a non-contact manner, and the condenser pipe is arranged to penetrate through the turntable and contacts a top surface of the tank.

18 Claims, 6 Drawing Sheets

(51) Int. Cl.
      B01D 3/34        (2006.01)
      B01D 5/00        (2006.01)
      C07H 13/04       (2006.01)

(56)              References Cited

U.S. PATENT DOCUMENTS

|  |  |  |  |  |  |
|---|---|---|---|---|---|
| 6,238,524 | B1 * | 5/2001 | Zebuhr | ................. | F28D 9/0043 |
|  |  |  |  |  | 202/172 |
| 6,908,533 | B2 * | 6/2005 | Zebuhr | ............... | B01D 5/0015 |
|  |  |  |  |  | 202/172 |
| 7,049,462 | B2 * | 5/2006 | Nagare | .................... | F28F 9/16 |
|  |  |  |  |  | 560/220 |
| 8,003,059 | B2 * | 8/2011 | Jachuck | ................... | C02F 1/30 |
|  |  |  |  |  | 422/198 |
| 9,073,959 | B2 * | 7/2015 | Micinski | ............... | C07H 13/04 |
| 10,350,508 | B2 * | 7/2019 | Campbell | ............. | B01D 1/223 |

| | | | | | |
|---|---|---|---|---|---|
| 2003/0132096 | A1 * | 7/2003 | Zebuhr | .................... | B01D 3/08 |
|  |  |  |  |  | 202/172 |
| 2009/0076261 | A1 * | 3/2009 | Xu | ......................... | C07H 13/02 |
|  |  |  |  |  | 536/127 |
| 2010/0288640 | A1 * | 11/2010 | Jachuck | ............... | B01J 19/1887 |
|  |  |  |  |  | 204/519 |
| 2011/0087019 | A1 * | 4/2011 | Micinski | ............... | C07H 13/04 |
|  |  |  |  |  | 536/122 |
| 2014/0367244 | A1 * | 12/2014 | Jachuck | ................... | B01D 1/22 |
|  |  |  |  |  | 159/13.1 |
| 2016/0271514 | A1 * | 9/2016 | Campbell | ............. | B01D 1/223 |
| 2021/0002317 | A1 * | 1/2021 | Zhou | ........................ | C07H 1/06 |

FOREIGN PATENT DOCUMENTS

| | | | |
|---|---|---|---|
| CN | 104774226 | A | 7/2015 |
| CN | 109575090 | A | 4/2019 |
| CN | 209317067 | U | 8/2019 |
| CN | 112218874 | A | 1/2021 |

* cited by examiner

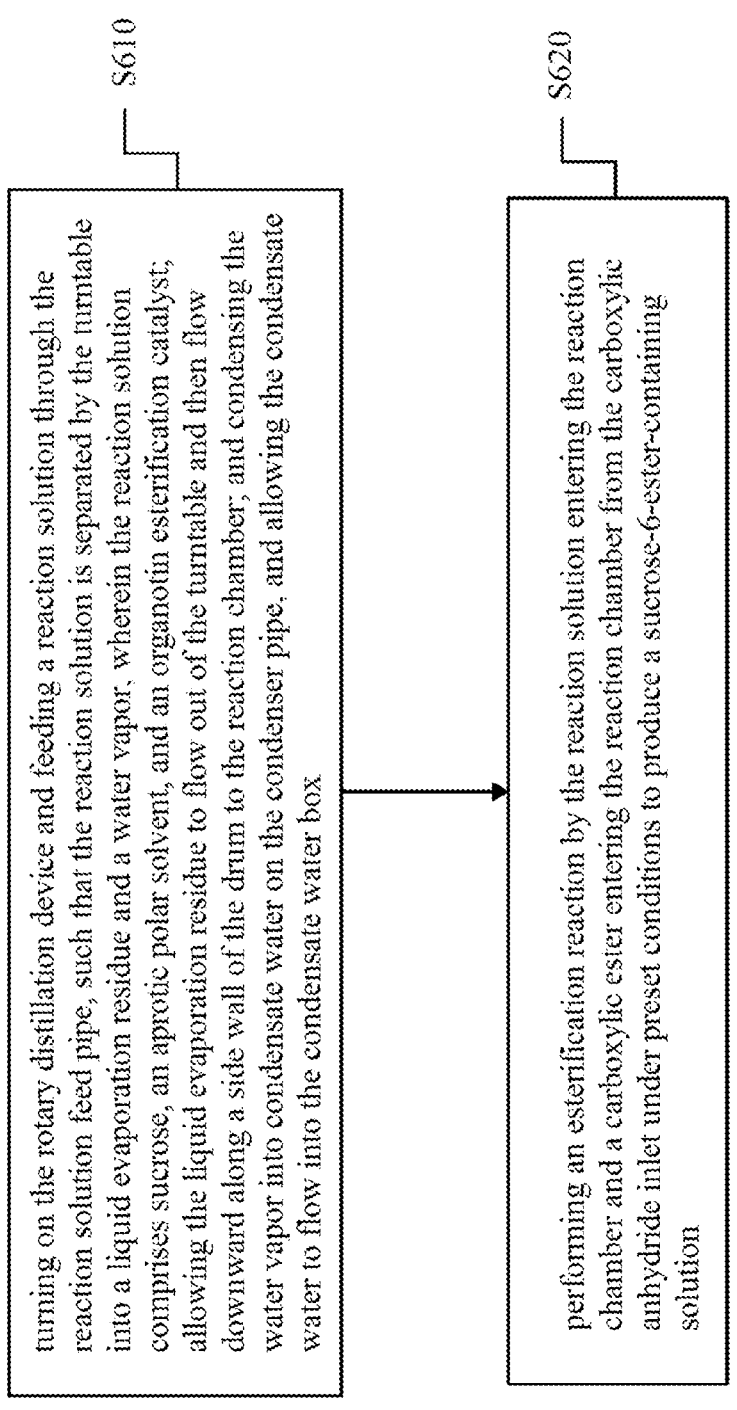

turning on the rotary distillation device and feeding a reaction solution through the reaction solution feed pipe, such that the reaction solution is separated by the turntable into a liquid evaporation residue and a water vapor, wherein the reaction solution comprises sucrose, an aprotic polar solvent, and an organotin esterification catalyst; allowing the liquid evaporation residue to flow out of the turntable and then flow downward along a side wall of the drum to the reaction chamber; and condensing the water vapor into condensate water on the condenser pipe, and allowing the condensate water to flow into the condensate water box

S610 performing an esterification reaction by the reaction solution entering the reaction chamber and a carboxylic ester entering the reaction chamber from the carboxylic anhydride inlet under preset conditions to produce a sucrose-6-ester-containing solution

PRODUCTION APPARATUS AND PRODUCTION METHOD OF SUCROSE-6-ESTER

TECHNICAL FIELD

The present disclosure belongs to the technical field of fine chemical industry, and in particular relates to a production apparatus and a production method of sucrose-6-ester.

BACKGROUND ART

Sucralose is a new sweetener with advantages such as high sweetness, no calories, high stability, and high safety, and has very promising market prospects. Sucralose-6-ester is an important intermediate in the production of sucralose.

In the prior art, a process for synthesizing sucrose-6-ester mainly includes: mixing sucrose, an aprotic polar solvent, and an organotin esterification catalyst to obtain a first reaction mixture; then bringing the first reaction mixture into contact with a gas or solvent vapor capable of removing water for a specified period of time at a specific temperature and pressure, such that the water in the first reaction mixture is removed to obtain a second reaction mixture; and then adding carboxylic anhydride to the second reaction mixture to obtain a third reaction mixture, and maintaining the third reaction mixture for a sufficient time to obtain the sucrose-6-ester. This process needs to use the gas or solvent vapor capable of removing water, which seriously affects the continuity of a production process of the sucrose-6-ester, prolongs the production cycle, and reduces the production efficiency. In addition, the consumption of a large amount of the gas or solvent capable of removing water greatly increases the production cost and energy consumption.

It should be noted that the statements herein merely provide background information related to the present disclosure and do not necessarily constitute the prior art.

SUMMARY

In view of the above problems, a production apparatus and a production method of sucrose-6-ester is provided in the present disclosure to overcome the above problems or at least partially solve the problems.

According to an aspect of the present disclosure, a production apparatus of sucrose-6-ester is provided, including a tank, a rotary distillation device, and a condensation device, where the tank includes a separation chamber and a reaction chamber that are arranged one above another and communicated with each other; the condensation device is sheathed inside the rotary distillation device, and the rotary distillation device is slidably connected in the separation chamber; a discharge port is formed at a lower end of the reaction chamber;

the rotary distillation device includes a drum and a turntable, the turntable is fixed on a top surface of the drum through a plurality of connecting plates, and a first heating device is provided on an outer wall of the turntable;

the condensation device includes a condenser pipe, a water receiving plate, and a condensate water box that are connected sequentially from top to bottom, the condensate water box is provided with a condensate water outlet pipe, and the condensate water outlet pipe extends to a position outside the tank;

the condensation device is sheathed inside the drum of the rotary distillation device in a non-contact manner, and the condenser pipe is arranged to penetrate through the turntable and contact with a top surface of the tank;

the tank is provided with a reaction solution feed pipe and a carboxylic ester feed pipe, and the reaction solution feed pipe penetrates through the top surface of the tank and extends to a bottom of the turntable; the carboxylic ester feed pipe penetrates through a side wall of the tank and extends to a position below the condensate water box; and the rotary distillation device is able to rotate along a central axis of the turntable to separate a reaction solution entering the rotary distillation device through the reaction solution feed pipe into a water vapor and a liquid evaporation residue.

Optionally, in the production apparatus described above, a part of a side wall of the drum opposite to the turntable is arranged to be inclined in a direction opposite to an inclination direction of a side wall of the turntable.

Optionally, in the production apparatus described above, a second heating device is provided on an outer surface of the part of the side wall of the drum arranged to be inclined.

Optionally, in the production apparatus described above, the condensation device further includes an annular condensation wall arranged to be inclined; and the condensation wall is arranged on the water receiving plate and is located between the outer wall of the turntable and an outer edge of the water receiving plate, and an inclination direction of the condensation wall is consistent with an inclination direction of the part of the side wall of the drum arranged to be inclined.

Optionally, in the production apparatus described above, a middle part of a side wall of the rotary distillation device and a bottom of the side wall of the rotary distillation device each are provided with an annular sliding block, an outer edge of the annular sliding block is inserted into an outer slide way on an inner wall of the tank, and an inner edge of the annular sliding block is inserted into an inner slide way on the side wall of the drum.

Optionally, in the production apparatus described above, the condensate water box is annular and is arranged close to the outer edge of the water receiving plate.

Optionally, in the production apparatus described above, the rotary distillation device is further provided with an annular baffle plate, a diameter of the annular baffle plate is smaller than a diameter of the drum, and the annular baffle plate is arranged below an opening of the carboxylic ester feed pipe and is fixedly connected to the drum through a plurality of connecting rods; and the carboxylic ester feed pipe and the condensate water outlet pipe are arranged to penetrate through a hollow portion of the annular baffle plate.

Optionally, in the production apparatus described above, the tank is further provided with a vacuum pipe, and the vacuum pipe is able to be connected to a vacuum pump.

Optionally, in the production apparatus described above, the reaction chamber is provided with a temperature control device.

According to another aspect of the present disclosure, a production method of sucrose-6-ester is provided, where the production method is implemented by the production apparatus described above and includes:

A step of reaction solution separation: turning on the rotary distillation device and feeding a reaction solution through the reaction solution feed pipe, such that the reaction solution is separated by the turntable into a liquid evaporation residue and a water vapor, wherein the reaction solution comprises sucrose, an aprotic polar solvent, and an organotin esterification catalyst; allowing the liquid evaporation residue to flow out of the turntable and then flow downward along a side wall of the drum to the reaction chamber; and condensing the water vapor into condensate water on the condenser pipe, and allowing the condensate water to flow into the condensate water box; and a step of esterification reaction: performing an esterification reaction by the reaction solution entering the reaction chamber and a carboxylic ester entering the reaction chamber from the carboxylic anhydride inlet under preset conditions to produce a sucrose-6-ester-containing solution.

In summary, the present disclosure has the following beneficial effects: with the rotary distillation device, a reaction solution can form a very thin liquid film on the inner wall of the turntable with the rotation of the turntable; a water vapor is fully separated and collected into the condensate water box along the condensation device to cool a liquid evaporation residue to make the liquid evaporation residue quickly reach a temperature of the esterification reaction, and the evaporation residue is spun out from the edge of the turntable to the inner wall of the drum under an action of a centrifugal force, flows downward along the inner wall of the drum, is thoroughly mixed with a carboxylic ester on the inner wall of the drum, and then enters the reaction chamber to undergo a esterification reaction to produce the target product sucrose-6-ester. The production apparatus of the present disclosure achieves the integration of distillation, cooling, mixing, and reaction steps of the preparation process of sucrose-6-ester, such that raw materials can be continuously fed into the production apparatus. The reaction solution separation step and the esterification reaction step are performed without interruption, such that the sucrose-6-ester can be continuously produced, which greatly shortens the production cycle, improves the production efficiency of the sucrose-6-ester, avoids the use of a large amount of a gas or solvent vapor capable of removing water during water removal of a raw reaction solution in the prior art, and overcomes the defects in the prior art such as high time consumption caused by the fact that the second reaction mixture needs to be pressed into another space and then mixed with a carboxylic anhydride. The production apparatus has a simple structure, a small floor space, and a low cost.

The above description is merely a summary of the technical solutions of the present disclosure. In order to allow the technical means of the present disclosure to be understood clearly and implemented in accordance with the content of the specification and allow the above and other objectives, features, and advantages of the present disclosure to be obvious and easy to understand, specific implementations of the present disclosure are described below.

BRIEF DESCRIPTION OF THE DRAWINGS

By reading the detailed description of the following preferred embodiments, various other advantages and benefits will become apparent to those of ordinary skill in the art. The accompanying drawings are provided merely to illustrate the preferred embodiments, rather than to limit the present disclosure. Throughout the accompanying drawings, the same reference numerals represent the same component. In the accompanying drawings:

FIG. 6 is a schematic flow chart of a production method of sucrose-6-ester according to an embodiment of the present disclosure.

DETAILED DESCRIPTION OF THE EMBODIMENTS

Exemplary embodiments of the present disclosure will be described in detail below with reference to the accompanying drawings. Although the accompanying drawings show exemplary embodiments of the present disclosure, it should be understood that the present disclosure may be implemented in various forms and should not be limited to the embodiments set forth herein. Instead, these embodiments are provided to provide a thorough understanding of the present disclosure, and fully convey a scope of the present disclosure to those skilled in the art.

The concept of the present disclosure is as follows: In the prior art, a reaction solution for producing sucrose-6-ester needs to first undergo water removal with a vapor or solvent in a reactor, and then is pressed into another reactor to react with a carboxylic anhydride to produce the sucrose-6-ester. In the above process, the water removal with the vapor or solvent requires a high energy consumption, bulky device, and a large floor space, and can only lead to insufficient water removal; after the water is removed, the reaction solution also needs to be pressed into another reactor to undergo an esterification reaction, which requires additional energy and time and reduces the production efficiency of the sucrose-6-ester; and the production mode in the prior art is discontinuous, and the next reaction can only be conducted after the previous reaction is completed, which also seriously affects the production efficiency of the sucrose-6-ester.

Figure 1:
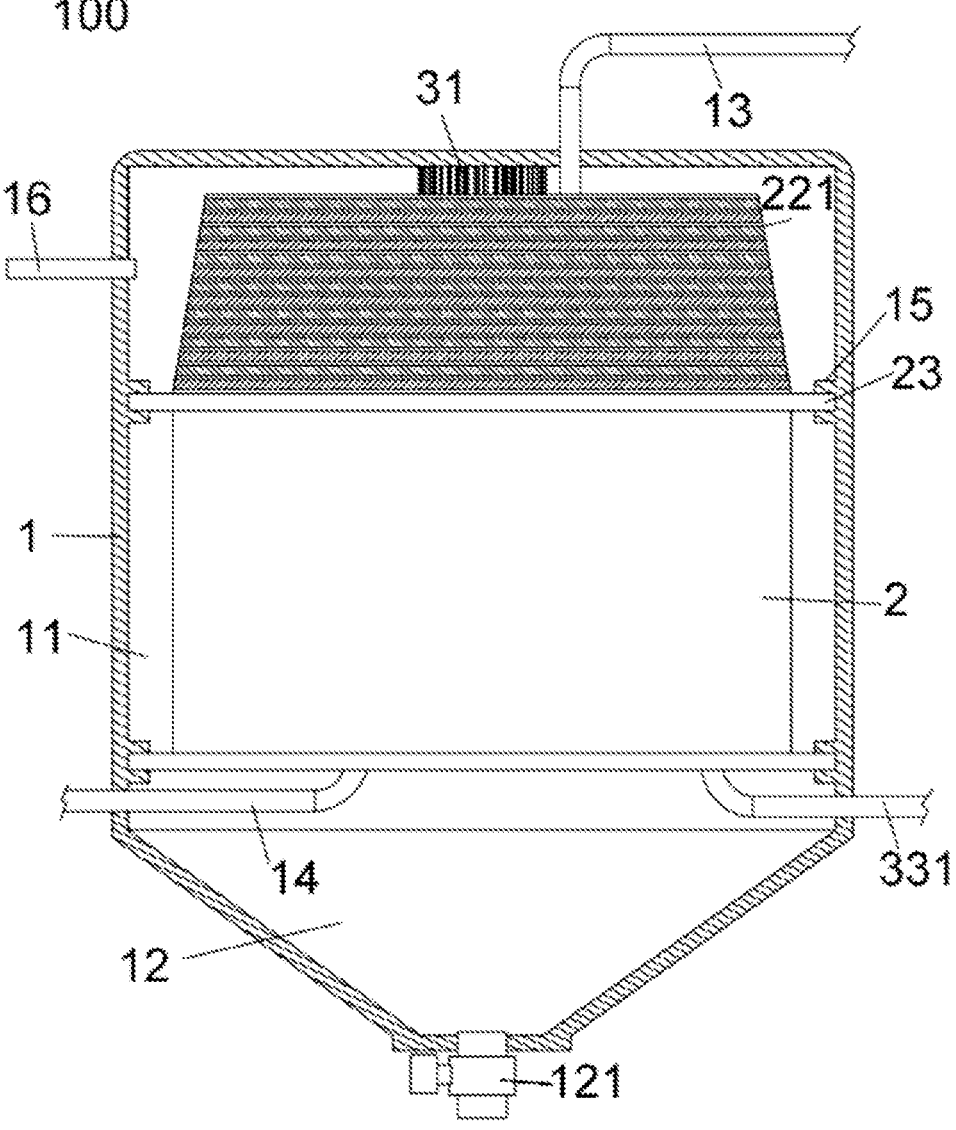
FIG. 1 is a side schematic diagram illustrating an overall external structure of a production apparatus of sucrose-6-ester according to an embodiment of the present disclosure.
Figure 2:
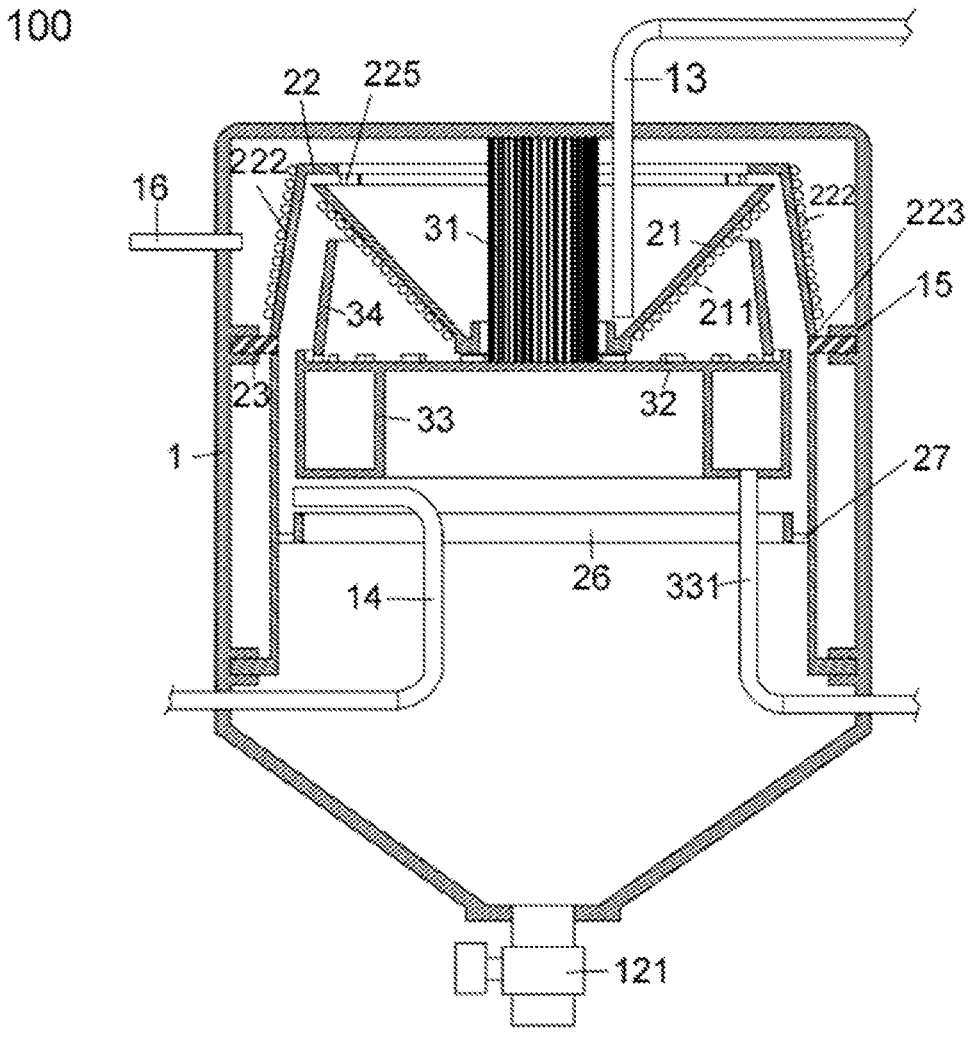
FIG. 2 is a three-dimensional schematic diagram illustrating sectional internal and external structures of the production apparatus of sucrose-6-ester according to an embodiment of the present disclosure.
Figure 3:
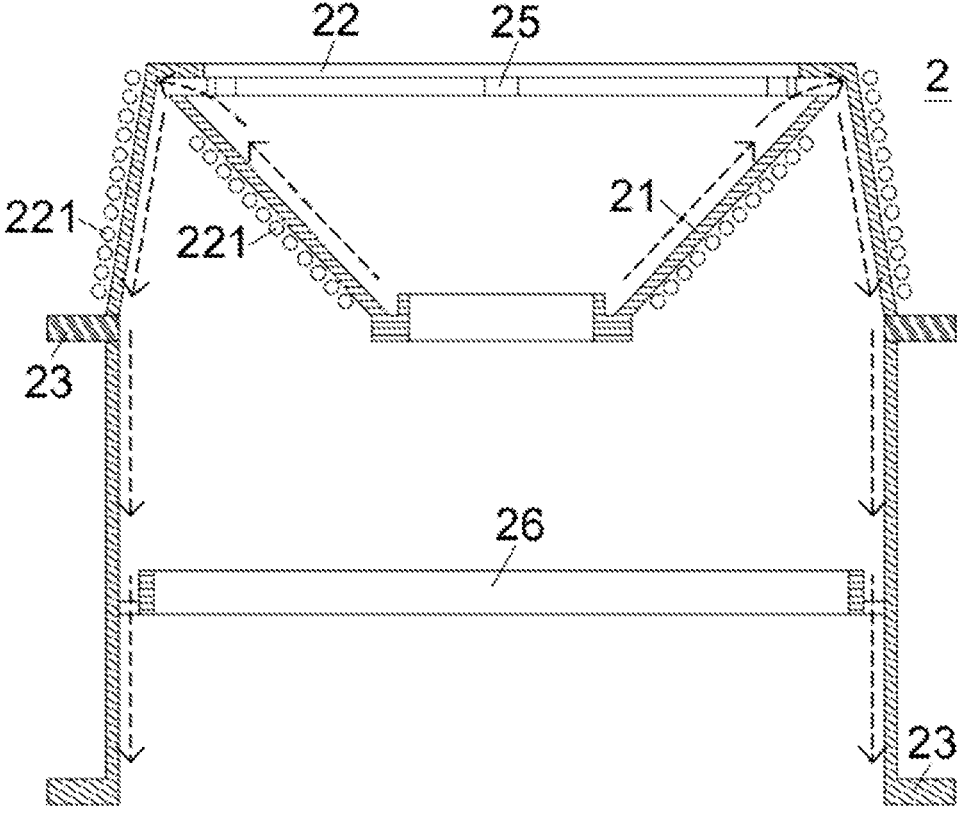
FIG. 3 is a schematic diagram illustrating sectional internal and external structures of a rotary distillation device of the production apparatus of sucrose-6-ester according to an embodiment of the present disclosure.
Figure 4:
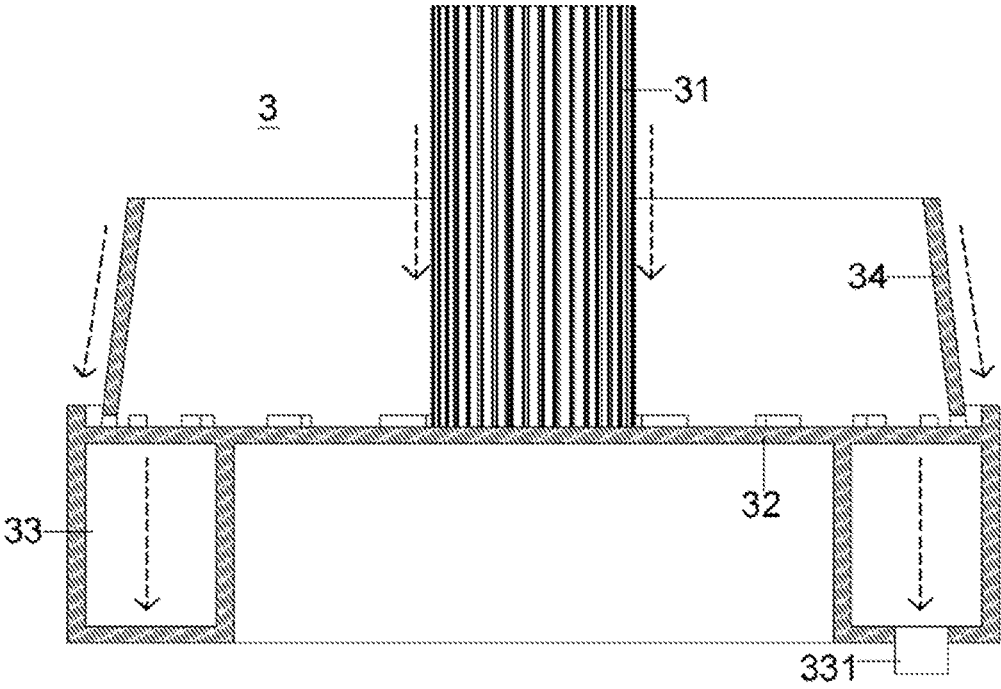
FIG. 4 is a schematic diagram illustrating cross-sectional structures of a condensation device of the production apparatus of sucrose-6-ester according to an embodiment of the present disclosure.

FIG. 1 is a side schematic diagram illustrating an overall external structure of a production apparatus of sucrose-6-ester according to an embodiment of the present disclosure; and FIG. 2 is a three-dimensional schematic diagram illustrating sectional internal and external structures of the production apparatus of sucrose-6-ester according to an embodiment of the present disclosure. FIG. 3 is a schematic diagram illustrating sectional internal and external structures of a rotary distillation device of the production apparatus of sucrose-6-ester according to an embodiment of the present disclosure; and FIG. 4 is a schematic diagram illustrating cross-sectional structures of a condensation device of the production apparatus of sucrose-6-ester according to an embodiment of the present disclosure.

As shown in FIG. 1 to FIG. 4, the production apparatus 100 of sucrose-6-ester is provided, including a tank 1, a rotary distillation device 2, and a condensation device 3, where the tank includes a separation chamber 11 and a reaction chamber 12 that are arranged one above another and communicated with each other; the condensation device 3 is sheathed inside the rotary distillation device 2, and the rotary distillation device 2 is slidably connected in the separation chamber 11; and a discharge port 121 is formed at a lower end of the reaction chamber 12.

It can be seen from FIG. 3 that the rotary distillation device 2 includes a drum 22 and a turntable 21, the turntable 21 is fixed on a top surface of the drum through a plurality of connecting plates 25, and a first heating device 211 is provided on an outer wall of the turntable 21.

It can be seen from FIG. 3 that there are large gaps between the plurality of connecting plates 25, which allow reaction solution in the turntable to flow out during the rotation of the turntable. In some embodiments of the present disclosure, the plurality of connecting plates 25 may be welded to top surfaces of the turntable 21 and the drum 22. In order to balance the drum and the turntable during rotation thereof, it is recommended that the drum and the turntable are coaxially arranged and a maximum diameter of the turntable 21 is smaller than an inner diameter of the top surface of the drum 22, which ensures that there is a gap between the turntable 21 and the drum to allow the reaction solution to flow out.

A first heating device 211 is provided on an outer wall of the turntable 21, and the first heating device 211 may heat a liquid film formed by the reaction solution in the turntable to increase an evaporation rate of water. The first heating device 211 may be, but is not limited to, a heating device consisting of an electric heating element and a water bath or oil bath heating element.

In some embodiments of the present disclosure, in order to make the reaction solution easy to store and move upward along a bottom surface of the turntable 21, a groove 212 may be formed at a bottom of aside wall of the turntable 21. When added to the turntable, the reaction solution can be temporarily stored in the groove 212. In some embodiments of the present disclosure, in order to make the water in the reaction solution thoroughly evaporated, a part of a side wall of the drum 22 opposite to the turntable 21 may be arranged to be inclined in a direction opposite to an inclination direction of a side wall of the turntable 21, which can be called a heating wall 222 herein; and a second heating device 221 is provided on an outer surface of the part of the side wall of the drum 22 arranged to be inclined. Under an action of a centrifugal force, the reaction solution moves upward along the side wall of the turntable from the groove 212 until it is spun out from the gaps between the plurality of connecting plates 25 at an edge of the turntable 21 to the side wall of the drum 22, and is heated once again at the heating wall 222 of the drum 22 for further evaporation and purification.

It can be seen from FIG. 4 that the condensation device 3 includes a condenser pipe 31, a water receiving plate 32, and a condensate water box 33 that are connected sequentially from top to bottom, the condensate water box 33 is provided with a condensate water outlet pipe 331, and the condensate water outlet pipe 331 extends to a position outside the tank 1.

The condenser pipe 31 may be, but is not limited to, a hollow metal pipe, and a plurality of fine condenser tubes with water or air as a medium are wrapped around a side wall of the condenser pipe 31, which may refer to other technical solutions in the prior art and is not limited in the present disclosure.

The water receiving plate 32 is closely arranged below the condenser pipe to receive condensate water flowing downward along the condenser pipe and guide the condensate water into the condensate water box 33. In some embodiments of the present disclosure, a plurality of guide slots (not shown in the figures) may be formed on an upper surface of the water receiving plate 32, and these guide slots may be connected to an inlet of the condensate water box 33 to guide the condensate water into the condensate water box 33.

The condensate water box 33 is arranged below and is connected to the water receiving plate to accommodate the condensate water, and the condensate water can cool the reaction solution with water removed by evaporation (namely, a fluid evaporation residue) that flows downward along the side wall of the drum 22, such that the evaporation residue reaches an appropriate temperature for the esterification reaction as soon as possible. The condensation device 3 is sheathed inside the drum of the rotary distillation device in a non-contact manner, and the condenser pipe 31 is arranged to penetrate through the turntable 21 and contacts a top surface of the tank 1.

The condensation device 3 does not contact an inner wall of the drum 22, and a specified space is left between the condensation device 3 and the inner wall of the drum 22, such that the evaporation residue can flow downward through the space. The condenser pipe 31 penetrates through a bottom surface of the turntable 21, and may be arranged without contact with the bottom surface of the turntable 21, that is, a small gap is left between the condenser pipe 31 and the bottom surface of the turntable 21 for the condensate water to flow downward. In the case that the groove 212 is formed on the bottom surface of the turntable 21, the condenser pipe 31 may be arranged with a gap relative to an inner side wall on which the groove 212 is formed.

The tank 1 is provided with a reaction solution feed pipe 13 and a carboxylic ester feed pipe 14, the reaction solution feed pipe 13 penetrates through the top surface of the tank 1 and extends to the bottom of the turntable 21, specifically may extend to the groove 212 at the bottom of the turntable 21. The carboxylic ester feed pipe 14 penetrates through a side wall of the tank 1 and extends to a position below the condensate water box 33.

It should be noted here that a bottom surface of the drum 22 is not closed, and the reaction solution feed pipe 13, the carboxylic ester feed pipe 14, and the condensate water outlet pipe 331 are fixedly arranged.

The rotary distillation device 2 can rotate along a central axis of the turntable 21, such that a reaction solution entering the rotary distillation device through the reaction solution feed pipe 13 is evaporated and separated into a water vapor and a liquid evaporation residue in the inner wall of the turntable 21 and further on the heating wall of the drum 22.

As shown in FIG. 2 and FIG. 4, in some embodiments of the present disclosure, the condensation device 3 further includes an annular condensation wall 34 arranged to be inclined; and the condensation wall 34 is arranged on the water receiving plate 32 and is located between the outer wall of the turntable 21 and an outer edge of the water receiving plate 32, and an inclination direction of the condensation wall is consistent with an inclination direction of the part of the side wall of the drum 22 arranged to be inclined.

In order to make condensate water produced on the part of the side wall of the drum 22 arranged to be inclined (namely, the heating wall 222) smoothly flow into the condensate water box 33, a condensation wall 34 may be provided surrounding the outer wall of the turntable 21 and is inclined in a direction consistent with an inclination direction of the heating wall 222.

As shown in FIG. 1 and FIG. 2, an annular sliding block 23 is provided at each of a middle part and a bottom of the side wall of the rotary distillation device 2, an outer edge of the annular sliding block 23 is inserted into an outer slide way 15 on an inner wall of the tank 1, and an inner edge of the annular sliding block 23 is inserted in an inner slide way 223 on the side wall of the drum 22.

The annular sliding block is provided to stabilize and fix the drum, and can rotate relative to the drum. Therefore, the drum can rotate freely at a high speed in the annular sliding block under the drive of a power device (not shown in the figures).

As shown in FIG. 2 and FIG. 4, in some embodiments of the present disclosure, the condensate water box 33 is annular and is arranged close to the outer edge of the water receiving plate 32. The above arrangement is provided to make the condensate water close to an inner side wall of the drum 22 to well cool the evaporation residue. Further, a bottom surface of the condensate water box 33 may be inclined, specifically, a side wall of the condensate water box close to the inner side wall of the drum 22 is longer than a side wall of the condensate water box far away from the inner side wall of the drum 22, which allows a better condensation effect.

As shown in FIG. 2, in some embodiments of the present disclosure, the rotary distillation device 2 is further provided with an annular baffle plate 26, a diameter of the annular baffle plate 26 is smaller than a diameter of the drum 22, and the annular baffle plate 26 is arranged below an opening of the carboxylic ester feed pipe 14 and is fixedly connected to the drum 22 through a plurality of connecting rods 27; and the carboxylic ester feed pipe 14 and the condensate water outlet pipe 331 are arranged to penetrate through a hollow portion of the annular baffle plate 26.

The annular baffle plate is provided to store a carboxylic anhydride entering the annular baffle plate through the carboxylic ester feed pipe 14; and the carboxylic anhydride is usually a powder, and thus is blown into the carboxylic ester feed pipe 14 through a pump and then sprayed from the opening of the carboxylic ester feed pipe 14 to the inner wall of the rotating drum 22 to be mixed with a fluid evaporation residue. However, a part of the powder may not be mixed with the fluid evaporation residue in time and falls to the annular baffle plate, and under an action of a centrifugal force, the part of the powder can still fly to the inner wall of the drum 22 to be mixed with the fluid evaporation residue.

As shown in FIG. 1 and FIG. 2, in some embodiments of the present disclosure, the tank body 1 is further provided with a vacuum pipe 16, and the vacuum pipe 16 can be connected to a vacuum pump (not shown in the figures). In order to make the water vapor well discharged out from the production device, the production device can also be depressurized. Specifically, the above purpose can be achieved via a vacuum pump connected to the vacuum pipe 16.

As shown in FIG. 1 and FIG. 2, in some embodiments of the present disclosure, the reaction chamber 12 is provided with a temperature control device (not shown in the figures). In order to make the esterification reaction proceed fast and smoothly, the reaction chamber 12 may be provided with the temperature control device. The esterification reaction may be conducted in the reaction chamber 12, or a separate esterification reactor may be connected to a discharge port 121 of the reaction chamber 12, which is not limited in the present disclosure.

Figure 5:
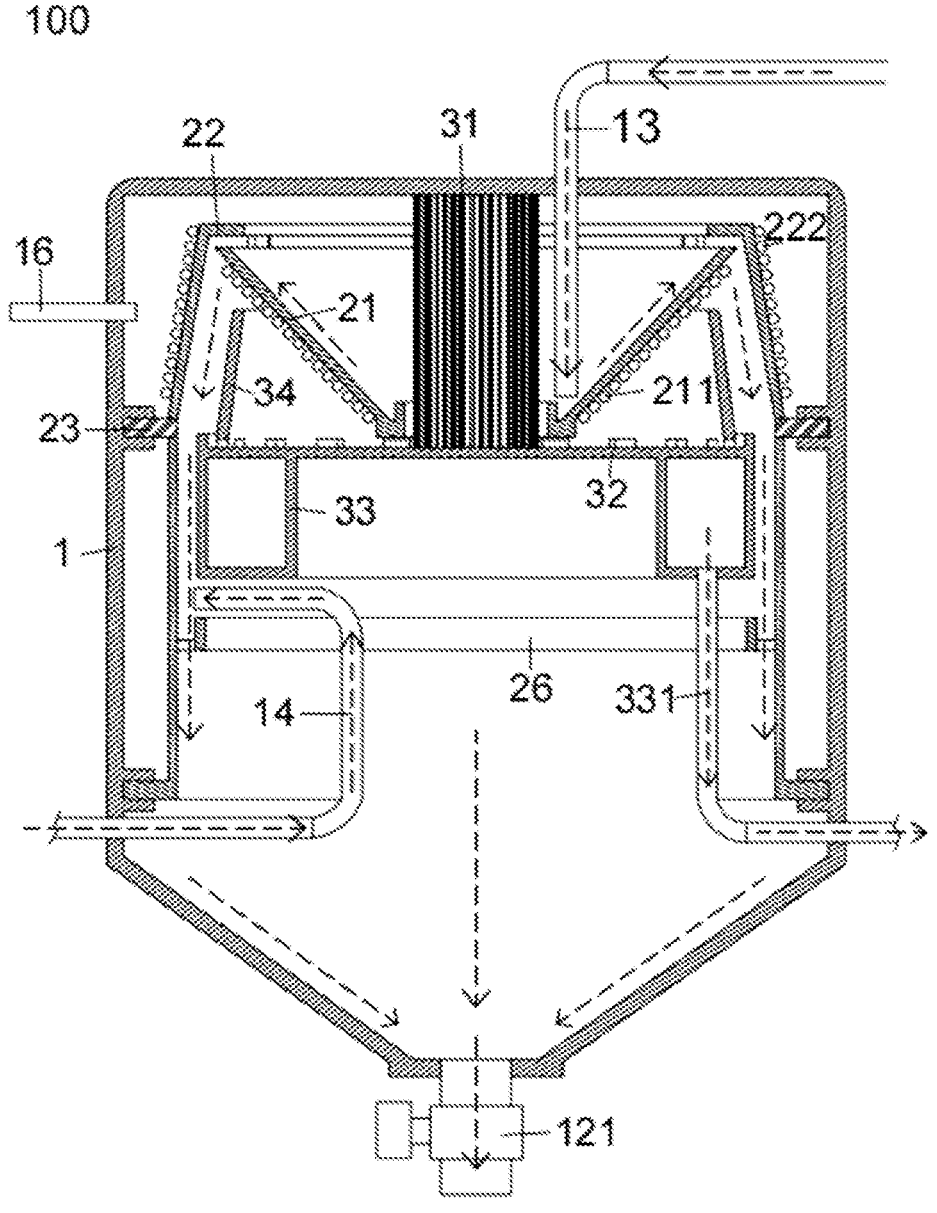
FIG. 5 is a schematic diagram illustrating material flow directions of the production apparatus of sucrose-6-ester according to an embodiment of the present disclosure.

FIG. 5 is a schematic diagram illustrating material flow directions of the production apparatus of sucrose-6-ester according to an embodiment of the present disclosure.

Arrows in FIG. 5 indicate the material flow directions. It can be seen from FIG. 5 that a reaction solution enters the groove 212 of the turntable 21 through the reaction solution feed pipe 13; with rotation of the turntable 21, the reaction solution undergoes evaporation while moving along the inner wall of the turntable 21 to the edge of the turntable 21, and then is spun out from the edge of the turntable 21 to the heating wall 222 of the drum 22, and then undergoes evaporation once again; resulting condensate water flows downward along the condenser pipe 31 and the condensation wall 34 to the water receiving plate 32, and then flows into the condensate water box 33; and a fluid evaporation residue flows downward along the inner wall of the drum 22 and is mixed with a carboxylic ester sprayed through the carboxylic ester feed pipe 14, and a resulting mixture flows into the reaction chamber 12 to undergo an esterification reaction in the reaction chamber and then flows out from the discharge port 121.

In the production apparatus of the present disclosure, with the rotary distillation device, a reaction solution can form a very thin liquid film on the inner wall of the turntable with the rotation of the turntable; a water vapor is fully separated and collected into the condensate water box along the condensation device to cool a fluid evaporation residue to make the evaporation residue quickly reach a temperature of the esterification reaction, and the fluid evaporation residue is spun out from the edge of the turntable to the inner wall of the drum under an action of a centrifugal force, flows downward along the inner wall of the drum, is thoroughly mixed with a carboxylic ester on the inner wall of the drum, and then enters the reaction chamber to undergo a esterification reaction to produce the target product sucrose-6-ester. The production device of the present disclosure achieves the integration of distillation, cooling, mixing, and reaction steps of the preparation process of sucrose-6-ester, such that raw materials can be continuously fed into the production device. The reaction solution separation step and the esterification reaction step are performed without interruption, such that the sucrose-6-ester can be continuously produced, which greatly shortens the production cycle, improves the production efficiency of the sucrose-6-ester, avoids the use of a large amount of gas or solvent vapor capable of removing water during water removal of a raw reaction solution in the prior art, and overcomes the defects in the prior art such as high time consumption caused by the fact that the second reaction mixture needs to be pressed into another space and then mixed with a carboxylic anhydride. The production device has a simple structure, a small floor space, and a low cost.

FIG. 6 is a schematic flow chart of a production method of sucrose-6-ester according to an embodiment of the present disclosure. The production method is implemented on the production apparatus described above, and at least includes the following steps S610 and S620:

reaction solution separation S610: turning on the rotary distillation device and feeding a reaction solution through the reaction solution feed pipe, such that the reaction solution is separated by the turntable into a liquid evaporation residue and a water vapor, wherein the reaction solution includes sucrose, an aprotic polar solvent, and an organotin esterification catalyst; allowing the evaporation residue to flow out of the turntable and then flow downward along the side wall of the drum to the reaction chamber and condensing the water vapor into condensate water on the condenser pipe, and allowing the condensate water to flow into the condensate water box; and esterification reaction S620: performing an esterification reaction by the reaction solution entering the reaction chamber and a carboxylic ester entering the reaction chamber from the carboxylic anhydride inlet under preset conditions to produce a sucrose-6-ester-containing solution.

In the production method described above, the present disclosure has no limitation on a rotational speed of the rotary distillation device. In some embodiments of the present disclosure, the rotational speed of the rotary distillation device may be 40 rpm to 200 rpm. If the rotational speed of the rotary distillation device is less than 40 rpm, it may be impossible to spin a reaction solution out from the turntable; and if the rotational speed of the rotary distillation device is greater than 200 rpm, the production apparatus should meet high requirements, a reaction solution can only undergo evaporation for a short time, and it may be impossible to thoroughly evaporate the water in the reaction solution, which is not conducive to the rapid production of sucrose-6-ester.

The raw materials and preset conditions for the esterification reaction in the above method are not limited, which can refer to the prior art and can also be adopted according to the following recommended technical solutions.

The present disclosure has no limitation on a type of the organotin compound, and a monotin organic compound or a bitin organic compound can be adopted. In some embodiments, the organotin compound is optionally any one or more selected from the group consisting of 1,3-dihydrocarbyloxy-1,1,3,3-tetra-(hydrocarbyl)distannoxane, tin di(hydrocarbyl)oxide, 1,3-diacyloxy-1,1,3,3-tetra-(hydrocarbyl)distannoxane, and 1-diacyloxy-1,1,3,3-tetra-(hydrocarbyl)distannoxane. In some other embodiments, the organotin compound is 1,3-diacyloxy-1,1,3,3-tetra-(hydrocarbyl)distannoxane; and in some other embodiments, the organotin compound is 1,3-diacetoxy-1,1,3,3-tetrabutyldistannoxane. The hydrocarbyloxy is optionally selected from the group consisting of alkoxy and phenoxy. In some embodiments, the alkoxy is optionally selected from the group consisting of methoxy, ethoxy, n-propoxy, n-butoxy, n-pentoxy, and n-hexoxy; and in some other embodiments, the alkoxy is methoxy. In some embodiments, the hydrocarbyl is optionally selected from the group consisting of alkyl, cycloalkyl, aryl, and aralkyl; in some other embodiments, the hydrocarbyl is alkyl; and in some other embodiments, the hydrocarbyl is normal-butyl.

The present disclosure has no limitation on a type of the aprotic polar solvent. In some embodiments, the aprotic polar solvent is any one or more selected from the group consisting of acetonitrile, 1,4-dioxane, methyl ethyl ketone, methyl isobutyl ketone, nitromethane, nitroethane, cyclohexanone, dimethyl sulfoxide, N-methylpyrrolidone, N,N-dimethylacetamide, hexamethylphosphoramide, and N,N-dimethylformamide; and in some other embodiments, the aprotic polar solvent is acetonitrile.

The present disclosure has no limitation on an amount of the aprotic polar solvent. In some embodiments, based on a mass of sucrose, a ratio of the mass of the solvent to the mass of sucrose is 2 to 20; in some other embodiments, the ratio of the mass of the solvent to the mass of sucrose is 3 to 10; and in some other embodiments, the ratio of the mass of the solvent to the mass of sucrose is 4 to 8.

The present disclosure has no limitation on a heating temperature for the heating chamber. In some embodiments, the heating temperature may be 65° C. to 150° C.; and in some other embodiments, the heating temperature may be 85° C. to 120° C.

The present disclosure has no limitation on, when the vacuum pipe is connected to the vacuum pump, a negative pressure in the production apparatus. In some embodiments, the negative pressure in the production apparatus may be maintained at 0.01 kPa to 50 kPa; and in some other embodiments, the negative pressure in the production apparatus may be maintained at 0.5 kPa to 20 kPa.

The present disclosure has no limitation on a type of the carboxylic anhydride, and the carboxylic anhydride is any one selected from the group consisting of acetic anhydride, butyric anhydride, benzoic anhydride, stearic anhydride, and lauric anhydride and is preferably acetic anhydride. The above types of organic acid anhydrides lead to the corresponding sucrose-6-carboxylates sucrose-6-acetate, sucrose-6-butyrate, sucrose-6-benzoate, sucrose-6-fatty acid ester, and sucrose-6-laurate. The sucrose-6-acetate and sucrose-6-benzoate can be used as raw materials for synthesizing other sucrose-6-carboxylates and can also be used as intermediates for synthesizing a sweetener sucralose; and the other types of sucrose-6-carboxylate can be used as food additives, chemical products, and synthetic intermediates for other reactions.

The present disclosure has no limitation on an amount of the carboxylic anhydride. In some embodiments, based on the mass of sucrose, a ratio of the mass of the carboxylic anhydride to the mass of the sucrose is 0.6 to 3.0; and in some other embodiments, the ratio of the mass of the carboxylic anhydride to the mass of the sucrose is 0.8 to 1.

The present disclosure has no limitation on the reaction conditions of the esterification reaction. In some embodiments, the esterification reaction may be conducted at 0° C. to 50° C.; and in some other embodiments, the esterification reaction may be conducted at 1° C. to 20° C. In some embodiments, the esterification reaction may be conducted for 10 min to 24 h; and in some other embodiments, the esterification reaction may be conducted for 30 min to 4 h.

It should be noted that reaction conditions, not exhaustively described above, may refer to the prior art.

Testing methods and reagent sources involved in the present disclosure are as follows:

High-Performance Liquid Chromatography (for Testing the Contents of Sucrose, Sucrose-6-Ester, and the Like in a Reaction Product)

High-performance liquid chromatograph of Shimadzu, Japan: RID-10A differential refractive index detection, LC-10ADVP high-pressure pump, and CTO-10ASVP incubator; chromatographic column: Agilent , XDB , C18 column (250 mm×4.6 mm, 5 μm); mobile phase: methanol-0.125% dipotassium phosphate (DKP) aqueous solution (4:6); column temperature: 30° C.; and flow rate: 1.0 m/min. Methanol (chromatographically pure), DKP (analytically pure), ultrapure water (UPW), and sucralose (purity: 99.9%) are required, and a content is determined by an external standard method.

Moisture Test Method

A moisture content is determined by the Karl Fischer method, which can refer to the prior art and will not be repeated in various examples.

Reagent Sources

The chemical reagents involved in the present disclosure and the raw material for preparing sucrose-6-ester may be commercially available, which are not limited in the present disclosure.

Example 1

Sucrose, an organotin esterification catalyst (1,1,3-diacetoxy-1,1,3,3-tetrabutyldistannoxane), and an aprotic polar solvent (DMF) were taken in a mass ratio of 1:2:10 and prepared into 300 kg of a reaction solution.

The production apparatus of sucrose-6-ester shown in FIG. 2 was used to produce sucrose-6-ester. The production apparatus was connected to the external vacuum pump.

The rotary distillation device was turned on such that the rotary distillation device rotated at 100 rpm; the reaction solution prepared above was continuously fed into the production apparatus at a rate of 4 m³/h; the reaction device was maintained at a negative pressure of 1 kPa and the first heating device 211, the second heating device 221, the condensation device 3, and the temperature control device of the reaction chamber were turned on.

With a mass ratio of sucrose to acetic anhydride being 1:1.1, the acetic anhydride was blown into the production apparatus through the carboxylic ester feed pipe at a temperature lower than 20° C. to allow an acylation reaction; and a sucrose-6-ester-containing product flowing out of the reaction product discharge port was collected.

A sample was taken from the evaporation residue before being mixed with the acetate and tested for a water content, and the water content in this example was lower than 500 ppm.

Water was added with a volume ratio of the water to the reaction system being 0.25:1 to perform a quenching reaction, and hexane was added with a volume ratio of the hexane to the reaction system being 1:1 to extract the organotin esterification catalyst to obtain a sucrose-6-acetate solution. A content of each substance was analyzed by the high-performance liquid chromatography. The normalization below and in the following examples means that, when a mixture is subjected to separation assay by the high-performance liquid chromatography, a sum of all substances is specified as 100%, and a percentage of each substance to all substances is determined according to a peak area. The product distribution was as follows:

a. sucrose-6-acetate: 86.97% (normalized);
b. diacetate: 8.26% (normalized); and
c. sucrose: 0.58% (normalized).

Example 2

Sucrose, an organotin esterification catalyst (1,1,3-diacetoxy-1,1,3,3-tetrabutyldistannoxane), and an aprotic polar solvent (DMF) were taken in a mass ratio of 1:2:10 and prepared into 500 kg of a reaction solution.

The production apparatus of sucrose-6-ester shown in FIG. 2 was used to produce a sucrose-6-ester. The production device was connected to the external vacuum pump.

The rotary distillation device was turned on such that the rotary distillation device rotated at 150 rpm; the reaction solution prepared above was continuously fed into the production apparatus at a rate of 6 m³/h; the reaction device was maintained at a negative pressure of 0.5 kPa and the first heating device 211, the second heating device 221, the condensation device 3, and the temperature control device of the reaction chamber were turned on.

With a mass ratio of sucrose to acetic anhydride being 1:1.1, the acetic anhydride was blown into the production apparatus through the carboxylic ester feed pipe at a temperature lower than 10° C. to allow an acylation reaction; and a sucrose-6-ester-containing product flowing out of the reaction product discharge port was collected.

A sample was taken from the evaporation residue before being mixed with the acetate and tested for a water content, and the water content in this example was lower than 500 ppm.

Water was added with a volume ratio of the water to the reaction system being 0.25:1 to perform a quenching reaction, and hexane was added with a volume ratio of the hexane to the reaction system being 1:1 to extract the organotin esterification catalyst to obtain a sucrose-6-acetate solution. A content of each substance was analyzed by the high-performance liquid chromatography. The normalization below and in the following examples means that, when a mixture is subjected to separation assay by the high-performance liquid chromatography, a sum of all substances is specified as 100%, and a percentage of each substance to all substances is determined according to a peak area. The product distribution was as follows:

a. sucrose-6-acetate: 89.50% (normalized);
b. diacetate: 7.55% (normalized); and
c. sucrose: 0.68% (normalized).

Example 3

Sucrose, an organotin esterification catalyst (1,1,3-diacetoxy-1,1,3,3-tetrabutyldistannoxane), and an aprotic polar solvent (DMF) were taken in a mass ratio of 1:2:10 and prepared into 300 kg of a reaction solution.

The production apparatus of sucrose-6-ester shown in FIG. 2 was used to produce a sucrose-6-ester. The production apparatus was connected to the external vacuum pump.

The rotary distillation device was turned on such that the rotary distillation device rotated at 200 rpm; the reaction solution prepared above was continuously fed into the production apparatus at a rate of 8 m³/h; the reaction device was maintained at a negative pressure of 0.5 kPa and the first heating device 211, the second heating device 221, the condensation device 3, and the temperature control device of the reaction chamber were turned on.

With a mass ratio of sucrose to acetic anhydride being 1:1.1, the acetic anhydride was blown into the production apparatus through the carboxylic ester feed pipe at a temperature lower than 15° C. to allow an acylation reaction; and a sucrose-6-ester-containing product flowing out of the reaction product discharge port was collected.

A sample was taken from the evaporation residue before being mixed with the acetate and tested for a water content, and the water content in this example was lower than 400 ppm.

Water was added with a volume ratio of the water to the reaction system being 0.25:1 to perform a quenching reaction, and hexane was added with a volume ratio of the hexane to the reaction system being 1:1 to extract the organotin esterification catalyst to obtain a sucrose-6-acetate solution. A content of each substance was analyzed by the high-performance liquid chromatography. The normalization below and in the following examples means that, when a mixture is subjected to separation assay by the high-performance liquid chromatography, a sum of all substances is specified as 100%, and a percentage of each substance to all substances is determined according to a peak area. The product distribution was as follows:

a. sucrose-6-acetate: 90.45% (normalized);
b. diacetate: 7.22% (normalized); and
c. sucrose: 0.24% (normalized).

Comparative Example 1

Sucrose, an organotin esterification catalyst (1,1,3-diacetoxy-1,1,3,3-tetrabutyldistannoxane), and an aprotic polar solvent (DMF) were taken in a mass ratio of 1:2:10 and prepared into 300 kg of a reaction solution, and the reaction solution was heated at 90° C. for dissolution to obtain a reaction mixed solution.

A packed tower was used for dehydration, and the packed tower had a diameter of 40 mm and was packed with a 3×8 glass spring packing at a packing height of 1 m, which was equivalent to 10-stage tower plates.

The reaction mixed solution prepared above was fed from an inlet at a top of the packed tower, with a negative pressure of 0.5 kPa; and a cyclohexane vapor (100° C., 4 atm) was fed from a gas inlet at a bottom of the packed tower. The reaction mixed solution and the cyclohexane vapor were in countercurrent contact to allow a reaction. A distillate (a vapor including cyclohexane, water, and DMF) discharged from the top of the packed tower was condensed, collected, dried to remove water, and then recycled.

A liquid sample was collected at the bottom of the packed tower, which was transparent and light-amber. A retention time of the reaction solution in a gas-liquid exchange reactor was about 1 min.

A sucrose content of a resulting solution was calculated to be 10%. The resulting solution was pressed into another reactor, then acetic anhydride was added at a temperature lower than 10° C. with a mass ratio of sucrose to acetic anhydride being 1:1.1 to allow an acylation reaction at a temperature lower than 10° C. for 2 h, and then water was added with a mass ratio of the water to a reaction solution being 0.25:1 to perform a quenching reaction; and cyclohexane was added with a mass ratio of the cyclohexane to the reaction solution being 1:1 to extract the organotin compound, and a resulting sucrose-6-acetate solution was analyzed by the high-performance liquid chromatography. Analysis results of the products were as follows:

a. sucrose-6-acetate: 72.05% (normalized);
    b. diacetate: 4.36% (normalized); and
    c. sucrose: 22.76% (normalized).

It can be seen from Examples 1 to 3 and Comparative Example 1 that, compared with the production apparatus using a packing in Comparative Example 1, the production apparatus provided in the present disclosure can lead to a high sucrose-6-carboxylate yield, a low side reaction occurrence probability, and a complete sucrose reaction. It can be known that the sucrose-6-acetate yield can reach 90.45% (normalized) in some examples of the present disclosure, but is only 72.05% (normalized) in Comparative Example 1, that is, the sucrose-6-carboxylate yield in the present disclosure is significantly higher than that in the prior art. Similarly, it can be seen from the diacetate and sucrose contents in the reaction products that the side reaction occurrence probability of the present disclosure is significantly reduced, and the conversion of sucrose in the present disclosure is more thorough.

In summary, the present disclosure has the following beneficial effects: with the rotary distillation device, a reaction solution can form a very thin liquid film on the inner wall of the turntable with the rotation of the turntable; a water vapor is fully separated and collected into the condensate water box along the condensation apparatus to cool a liquid evaporation residue to make the liquid evaporation residue quickly reach a temperature of the esterification reaction, and the liquid evaporation residue is spun out from the edge of the turntable to the inner wall of the drum under an action of a centrifugal force, flows downward along the inner wall of the drum, is thoroughly mixed with a carboxylic ester on the inner wall of the drum, and then enters the reaction chamber to undergo an esterification reaction to produce the target product sucrose-6-ester. The production device of the present disclosure achieves the integration of distillation, cooling, mixing, and reaction steps of the preparation process of sucrose-6-ester, such that raw materials can be continuously fed into the production apparatus. The reaction solution separation step and the esterification reaction step are performed without interruption, such that the sucrose-6-ester can be continuously produced, which greatly shortens the production cycle, improves the production efficiency of the sucrose-6-ester, avoids the use of a large amount of gas or solvent vapor capable of removing water during water removal of a raw reaction solution in the prior art, and overcomes the defects in the prior art such as high time consumption caused by the fact that the second reaction mixture needs to be pressed into another space and then mixed with a carboxylic anhydride. The production apparatus has a simple structure, a small floor space, and a low cost.

The above are merely specific implementations of the present disclosure, and under the above instruction of the present disclosure, those skilled in the art may make other improvements or variations on the basis of the above examples. Those skilled in the art should understand that the above specific description is merely intended to well explain the purpose of the present disclosure, and a scope of the present disclosure shall be subject to the scope of the claims.

In addition, those skilled in the art can understand that, although some examples herein include some features included in other examples but no other features, a combination of features of different examples falls within the scope of the present disclosure and forms a different example. For example, in the claims, any one of the claimed examples can be used in any combination.

What is claimed is:

1. A production apparatus of sucrose-6-ester, comprising:
    a tank,
    a rotary distillation device, and
    a condensation device,
    wherein the tank comprises a separation chamber and a reaction chamber that are arranged one above another and communicated with each other; the condensation device is sheathed inside the rotary distillation device, and the rotary distillation device is slidably connected in the separation chamber; a discharge port is formed at a lower end of the reaction chamber;
    the rotary distillation device comprises a drum and a turntable, the turntable is fixed on a top surface of the drum through a plurality of connecting plates, and a first heating device is provided on an outer wall of the turntable;
    the condensation device comprises a condenser pipe, a water receiving plate, and a condensate water box that are connected sequentially from top to bottom, the condensate water box is provided with a condensate water outlet pipe, and the condensate water outlet pipe extends to a position outside the tank;
    the condensation device is sheathed inside the drum of the rotary distillation device in a non-contact manner, the condenser pipe is arranged to penetrate through a bottom of the turntable and contact with a top surface of the tank, and the condenser pipe is spaced from the bottom of the turntable;
    the tank is provided with a reaction solution feed pipe and a carboxylic ester feed pipe, and the reaction solution feed pipe penetrates through the top surface of the tank and extends to a bottom of the turntable; the carboxylic ester feed pipe penetrates through a side wall of the tank and extends to a position below the condensate water box; and the rotary distillation device is configured to rotate along a central axis of the turntable to separate a reaction solution entering the rotary distillation device through the reaction solution feed pipe into a water vapor and a liquid evaporation residue and spin the liquid evaporation residue onto an inner side wall of the drum, such that the liquid evaporation residue flows downward along the inner side wall of the drum, the condenser pipe is configured to condense the water vapor into water, such that the water flows downward along the condenser pipe and is guided into the condensate water box via the water receiving plate, the water accommodated in the condensate water box is configured to cool the liquid evaporation residue flowing downward along the inner side wall of the drum.

2. The production apparatus according to claim 1, wherein a part of a side wall of the drum opposite to the turntable is arranged to be inclined in a direction opposite to an inclination direction of a side wall of the turntable.

3. The production apparatus according to claim 2, wherein a second heating device is provided on an outer surface of the part of the side wall of the drum arranged to be inclined.

4. The production apparatus according to claim 2, wherein the condensation device further comprises an annular condensation wall arranged to be inclined; and the condensation wall is arranged on the water receiving plate and is located between an outer wall of the turntable and an outer edge of the water receiving plate, and an inclination direction of the condensation wall is consistent with an inclination direction of the part of the side wall of the drum arranged to be inclined.

5. The production apparatus according to claim 1, wherein a middle part of a side wall of the rotary distillation device and a bottom of the side wall of the rotary distillation device each are provided with an annular sliding block, an outer edge of the annular sliding block is inserted into an outer slide way on an inner wall of the tank, and an inner edge of the annular sliding block is inserted into an inner slide way on the side wall of the drum.

6. The production apparatus according to claim 1, wherein the condensate water box is annular and is arranged close to an outer edge of the water receiving plate.

7. The production apparatus according to claim 1, wherein the rotary distillation device is further provided with an annular baffle plate, a diameter of the annular baffle plate is smaller than a diameter of the drum, and the annular baffle plate is arranged below an opening of the carboxylic ester feed pipe and is fixedly connected to the drum through a plurality of connecting rods; and the carboxylic ester feed pipe and the condensate water outlet pipe are arranged to penetrate through a hollow portion of the annular baffle plate.

8. The production apparatus according to claim 1, wherein the tank is further provided with a vacuum pipe, and the vacuum pipe is configured to be connected to a vacuum pump.

9. The production apparatus according to claim 1, wherein the reaction chamber is provided with a temperature control device.

10. A production method of sucrose-6-ester, wherein the production method is implemented by the production apparatus according to claim 1, and the production method comprising:

a step of reaction solution separation: turning on the rotary distillation device and feeding a reaction solution through the reaction solution feed pipe, such that the reaction solution is separated by the turntable into a liquid evaporation residue and a water vapor, wherein the reaction solution comprises sucrose, an aprotic polar solvent, and an organotin esterification catalyst; allowing the liquid evaporation residue to flow out of the turntable and then flow downward along a side wall of the drum to the reaction chamber; and condensing the water vapor into condensate water on the condenser pipe, and allowing the condensate water to flow into the condensate water box; and a step of esterification reaction: performing an esterification reaction by the reaction solution entering the reaction chamber and a carboxylic ester entering the reaction chamber from the carboxylic anhydride inlet under preset conditions to produce a sucrose-6-ester-containing solution.

11. A production method of sucrose-6-ester, wherein the production method is implemented by the production apparatus according to claim 2, and the production method comprising:

a step of reaction solution separation: turning on the rotary distillation device and feeding a reaction solution through the reaction solution feed pipe, such that the reaction solution is separated by the turntable into a liquid evaporation residue and a water vapor, wherein the reaction solution comprises sucrose, an aprotic polar solvent, and an organotin esterification catalyst; allowing the liquid evaporation residue to flow out of the turntable and then flow downward along a side wall of the drum to the reaction chamber; and condensing the water vapor into condensate water on the condenser pipe, and allowing the condensate water to flow into the condensate water box; and a step of esterification reaction: performing an esterification reaction by the reaction solution entering the reaction chamber and a carboxylic ester entering the reaction chamber from the carboxylic anhydride inlet under preset conditions to produce a sucrose-6-ester-containing solution.

12. A production method of sucrose-6-ester, wherein the production method is implemented by the production apparatus according to claim 3, and the production method comprising:

a step of reaction solution separation: turning on the rotary distillation device and feeding a reaction solution through the reaction solution feed pipe, such that the reaction solution is separated by the turntable into a liquid evaporation residue and a water vapor, wherein the reaction solution comprises sucrose, an aprotic polar solvent, and an organotin esterification catalyst; allowing the liquid evaporation residue to flow out of the turntable and then flow downward along a side wall of the drum to the reaction chamber; and condensing the water vapor into condensate water on the condenser pipe, and allowing the condensate water to flow into the condensate water box; and a step of esterification reaction: performing an esterification reaction by the reaction solution entering the reaction chamber and a carboxylic ester entering the reaction chamber from the carboxylic anhydride inlet under preset conditions to produce a sucrose-6-ester-containing solution.

13. A production method of sucrose-6-ester, wherein the production method is implemented by the production apparatus according to claim 4, and the production method comprising:

a step of reaction solution separation: turning on the rotary distillation device and feeding a reaction solution through the reaction solution feed pipe, such that the reaction solution is separated by the turntable into a liquid evaporation residue and a water vapor, wherein the reaction solution comprises sucrose, an aprotic polar solvent, and an organotin esterification catalyst; allowing the liquid evaporation residue to flow out of the turntable and then flow downward along a side wall of the drum to the reaction chamber; and condensing the water vapor into condensate water on the condenser pipe, and allowing the condensate water to flow into the condensate water box; and a step of esterification reaction: performing an esterification reaction by the reaction solution entering the reaction chamber and a carboxylic ester entering the reaction chamber from the carboxylic anhydride inlet under preset conditions to produce a sucrose-6-ester-containing solution.

14. A production method of sucrose-6-ester, wherein the production method is implemented by the production apparatus according to claim 5, and the production method comprising:

a step of reaction solution separation: turning on the rotary distillation device and feeding a reaction solution through the reaction solution feed pipe, such that the reaction solution is separated by the turntable into a liquid evaporation residue and a water vapor, wherein the reaction solution comprises sucrose, an aprotic polar solvent, and an organotin esterification catalyst; allowing the liquid evaporation residue to flow out of the turntable and then flow downward along a side wall of the drum to the reaction chamber; and condensing the water vapor into condensate water on the condenser pipe, and allowing the condensate water to flow into the condensate water box; and a step of esterification reaction: performing an esterification reaction by the reaction solution entering the reaction chamber and a carboxylic ester entering the reaction chamber from the carboxylic anhydride inlet under preset conditions to produce a sucrose-6-ester-containing solution.

15. A production method of sucrose-6-ester, wherein the production method is implemented by the production apparatus according to claim 6, and the production method comprising:

a step of reaction solution separation: turning on the rotary distillation device and feeding a reaction solution through the reaction solution feed pipe, such that the reaction solution is separated by the turntable into a liquid evaporation residue and a water vapor, wherein the reaction solution comprises sucrose, an aprotic polar solvent, and an organotin esterification catalyst; allowing the liquid evaporation residue to flow out of the turntable and then flow downward along a side wall of the drum to the reaction chamber; and condensing the water vapor into condensate water on the condenser pipe, and allowing the condensate water to flow into the condensate water box; and a step of esterification reaction: performing an esterification reaction by the reaction solution entering the reaction chamber and a carboxylic ester entering the reaction chamber from the carboxylic anhydride inlet under preset conditions to produce a sucrose-6-ester-containing solution.

16. A production method of sucrose-6-ester, wherein the production method is implemented by the production apparatus according to claim 7, and the production method comprising:

a step of reaction solution separation: turning on the rotary distillation device and feeding a reaction solution through the reaction solution feed pipe, such that the reaction solution is separated by the turntable into a liquid evaporation residue and a water vapor, wherein the reaction solution comprises sucrose, an aprotic polar solvent, and an organotin esterification catalyst; allowing the liquid evaporation residue to flow out of the turntable and then flow downward along a side wall of the drum to the reaction chamber; and condensing the water vapor into condensate water on the condenser pipe, and allowing the condensate water to flow into the condensate water box; and a step of esterification reaction: performing an esterification reaction by the reaction solution entering the reaction chamber and a carboxylic ester entering the reaction chamber from the carboxylic anhydride inlet under preset conditions to produce a sucrose-6-ester-containing solution.

17. A production method of sucrose-6-ester, wherein the production method is implemented by the production apparatus according to claim 8, and the production method comprising:

a step of reaction solution separation: turning on the rotary distillation device and feeding a reaction solution through the reaction solution feed pipe, such that the reaction solution is separated by the turntable into a liquid evaporation residue and a water vapor, wherein the reaction solution comprises sucrose, an aprotic polar solvent, and an organotin esterification catalyst; allowing the liquid evaporation residue to flow out of the turntable and then flow downward along a side wall of the drum to the reaction chamber; and condensing the water vapor into condensate water on the condenser pipe, and allowing the condensate water to flow into the condensate water box; and a step of esterification reaction: performing an esterification reaction by the reaction solution entering the reaction chamber and a carboxylic ester entering the reaction chamber from the carboxylic anhydride inlet under preset conditions to produce a sucrose-6-ester-containing solution.

18. A production method of sucrose-6-ester, wherein the production method is implemented by the production apparatus according to claim 9, and the production method comprising:

a step of reaction solution separation: turning on the rotary distillation device and feeding a reaction solution through the reaction solution feed pipe, such that the reaction solution is separated by the turntable into a liquid evaporation residue and a water vapor, wherein the reaction solution comprises sucrose, an aprotic polar solvent, and an organotin esterification catalyst; allowing the liquid evaporation residue to flow out of the turntable and then flow downward along a side wall of the drum to the reaction chamber; and condensing the water vapor into condensate water on the condenser pipe, and allowing the condensate water to flow into the condensate water box; and a step of esterification reaction: performing an esterification reaction by the reaction solution entering the reaction chamber and a carboxylic ester entering the reaction chamber from the carboxylic anhydride inlet under preset conditions to produce a sucrose-6-ester- containing solution.

\* \* \* \* \*